(12) United States Patent
Chishima

(10) Patent No.: US 11,905,608 B2
(45) Date of Patent: Feb. 20, 2024

(54) FUEL PRODUCTION SYSTEM

(71) Applicant: Honda Motor Co., Ltd., Tokyo (JP)

(72) Inventor: Hiroshi Chishima, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 17/831,674

(22) Filed: Jun. 3, 2022

(65) Prior Publication Data
US 2022/0401909 A1 Dec. 22, 2022

(30) Foreign Application Priority Data
Jun. 7, 2021 (JP) ................................. 2021-094872

(51) Int. Cl.
| | | |
|---|---|---|
| C07C 29/151 | (2006.01) | |
| C07C 31/04 | (2006.01) | |
| C25B 15/02 | (2021.01) | |
| C25B 15/08 | (2006.01) | |
| C25B 1/04 | (2021.01) | |
| B01J 19/00 | (2006.01) | |
| B01J 19/24 | (2006.01) | |

(52) U.S. Cl.
CPC .......... *C25B 15/02* (2013.01); *C07C 29/1518* (2013.01); *C25B 1/04* (2013.01); *C25B 15/081* (2021.01); *B01J 19/004* (2013.01); *B01J 19/245* (2013.01); *B01J 2219/0004* (2013.01); *C10J 2300/1665* (2013.01); *C10J 2300/1684* (2013.01); *Y02E 60/36* (2013.01); *Y02P 20/133* (2015.11)

(58) Field of Classification Search
CPC ........ C10J 2300/0966; C10J 2300/1284; C10J 2300/1292; C10J 2300/1684
See application file for complete search history.

(56) References Cited

U.S. PATENT DOCUMENTS

| | | | | |
|---|---|---|---|---|
| 6,308,465 | B1* | 10/2001 | Galloway | ......... H01M 8/04216 52/220.3 |
| 11,566,192 | B2* | 1/2023 | Chishima | .................. C25B 1/04 |
| 11,608,475 | B2* | 3/2023 | Chishima | ................. C10K 1/08 |
| 2001/0054256 | A1* | 12/2001 | Katayama | .................. C10J 3/16 48/210 |

(Continued)

FOREIGN PATENT DOCUMENTS

JP 2002193858 A 7/2002

*Primary Examiner* — Jennifer A Leung
(74) *Attorney, Agent, or Firm* — Duft & Bornsen, PC

(57) ABSTRACT

Fuel production system includes: synthesis gas generation unit configured to generate synthesis gas containing hydrogen and carbon monoxide from carbon-containing raw material; fuel production unit configured to produce fuel from synthesis gas generated; water electrolyzer configured to electrolyze water to generate water-electrolyzed hydrogen; hydrogen supply unit configured to supply water-electrolyzed hydrogen generated to synthesis gas generation unit; and controller. The controller is configured to perform: calculating input energy based on first energy possessed by raw material, second energy consumed by water electrolyzer, third energy consumed by synthesis gas generation unit, and fourth energy consumed by fuel production unit; calculating recovered energy based on fifth energy possessed by fuel produced; and controlling water electrolyzer based on input energy and recovered energy calculated.

5 Claims, 5 Drawing Sheets

(56) References Cited

U.S. PATENT DOCUMENTS

| | | | | |
|---|---|---|---|---|
| 2011/0185634 A1* | 8/2011 | Prestel | .................... | C10K 1/08 |
| | | | | 422/186.04 |
| 2021/0292664 A1* | 9/2021 | Chishima | ................... | C10J 3/00 |
| 2022/0403536 A1* | 12/2022 | Chishima | .............. | C07C 29/152 |

* cited by examiner

FUEL PRODUCTION SYSTEM

CROSS-REFERENCE TO RELATED APPLICATION

This application is based upon and claims the benefit of priority from Japanese Patent Application No. 2021-094872 filed on Jun. 7, 2021, the content of which is incorporated herein by reference.

BACKGROUND OF THE INVENTION

Field of the Invention

This invention relates to a fuel production system configured to produce fuel by electrolyzing water.

Description of the Related Art

Conventionally, as this type of apparatus, apparatuses are known that produce methanol using biomass as raw material (for example, Japanese Unexamined Patent Publication No. 2002-193858 (JP2002-193858A)). The apparatus described in JP2002-193858A electrolyzes water to generate hydrogen by solar power and wind power, and replenishes this hydrogen into a gas containing carbon monoxide and hydrogen obtained by gasifying biomass, whereby adjusting the ratio of the carbon monoxide and the hydrogen to a ratio suitable for methanol synthesis.

However, as the apparatus described in JP2002-193858A, when producing fuel by utilizing renewable power such as solar power or wind power, although carbon emissions can be reduced, there is a risk of increasing energy loss and fuel production costs.

SUMMARY OF THE INVENTION

An aspect of the present invention is a fuel production system, including: a synthesis gas generation unit configured to generate synthesis gas containing hydrogen and carbon monoxide from carbon-containing raw material; a fuel production unit configured to produce fuel from the synthesis gas generated by the synthesis gas generation unit; a water electrolyzer configured to electrolyze water to generate water-electrolyzed hydrogen; a hydrogen supply unit configured to supply the water-electrolyzed hydrogen generated by the water electrolyzer to the synthesis gas generation unit; and a controller including an arithmetic unit and a storage unit. The controller is configured to perform: calculating an input energy based on a first energy possessed by the carbon-containing raw material, a second energy consumed by the water electrolyzer when generating the water-electrolyzed hydrogen, a third energy consumed by the synthesis gas generation unit when generating the synthesis gas, and a fourth energy consumed by the fuel production unit when producing the fuel; calculating a recovered energy based on a fifth energy possessed by the fuel produced by the fuel production unit; and controlling the water electrolyzer based on the input energy and the recovered energy calculated.

BRIEF DESCRIPTION OF THE DRAWINGS

The objects, features, and advantages of the present invention will become clearer from the following description of embodiments in relation to the attached drawings, in which.

DETAILED DESCRIPTION OF THE INVENTION

An embodiment of the present invention is explained with reference to FIGS. 1 to 7 in the following. A fuel production system according to the embodiment of the present invention electrolyzes water by renewable power such as solar power or wind power to generate hydrogen (water-electrolyzed hydrogen), and uses this water-electrolyzed hydrogen to produce so-called electrosynthetic fuel (e-fuel) from carbon-containing raw materials such as biomass. In the following, an example will be explained in particular in which biomass is gasified to generate a synthesis gas containing hydrogen and carbon monoxide, and a methanol fuel is produced from the generated synthesis gas.

Figure 1:
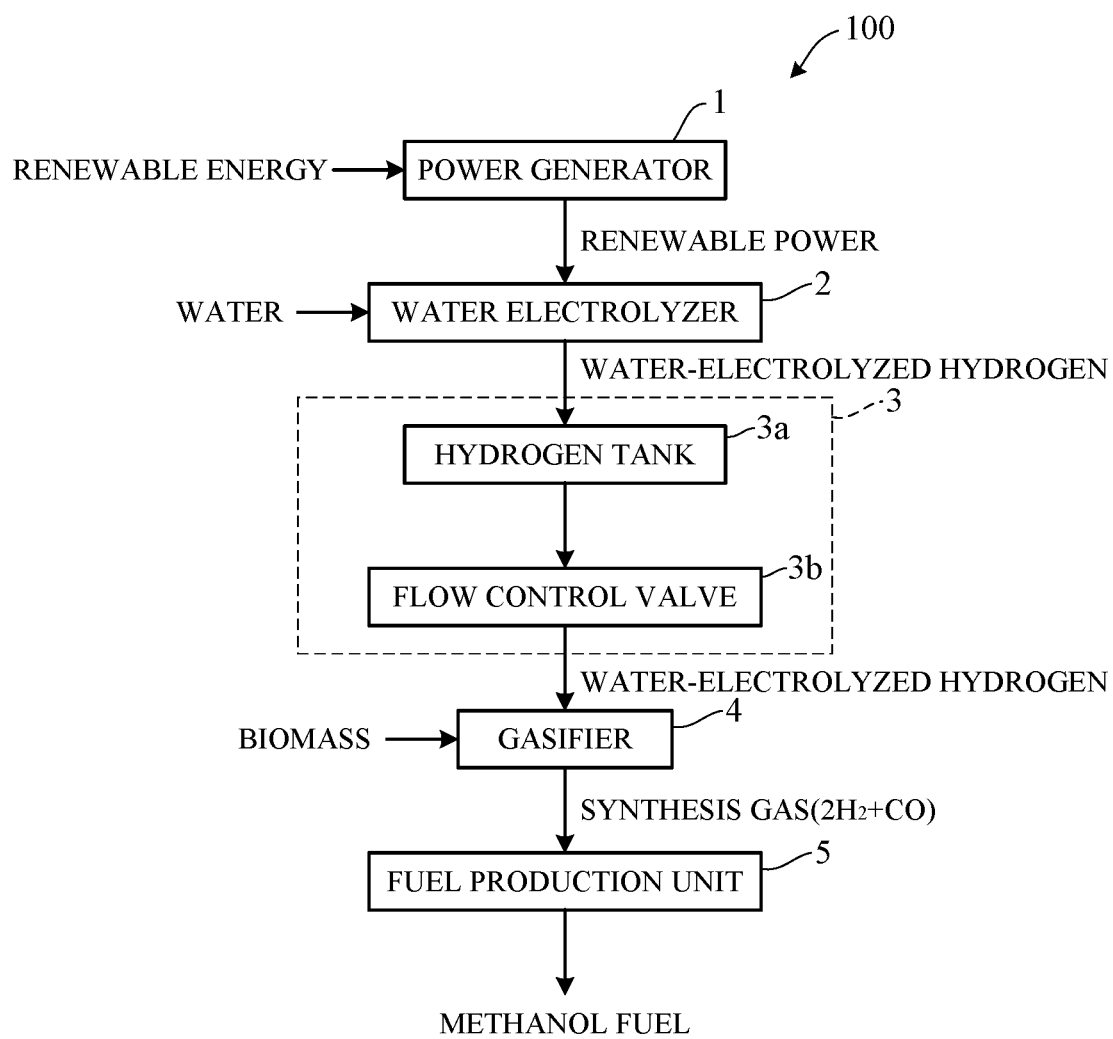
FIG. 1 is a block diagram schematically showing an example of overall configuration of a fuel production system according to an embodiment of the present invention.

FIG. 1 is a block diagram schematically showing an example of overall configuration of a fuel production system 100 according to the embodiment of the present invention. As shown in FIG. 1, the fuel production system 100 includes a power generator 1, a water electrolyzer 2, a hydrogen supply unit 3, a gasifier 4, and a fuel production unit 5.

The power generator 1 is configured, for example, as a solar power generator that converts solar energy into electrical energy using semiconductor devices or a wind power generator that converts wind energy into electrical energy using a windmill, and generates renewable power. The renewable power generated by the power generator 1 is supplied to the water electrolyzer 2, the hydrogen supply unit 3, the gasifier 4, and the fuel production unit 5.

The water electrolyzer 2 generates water-electrolyzed hydrogen by electrolyzing water using the renewable power generated by the power generator 1. The water electrolyzer 2 is provided with sensors that measure an electrolysis voltage of the water electrolyzer 2, a power consumption of the water electrolyzer 2, a generation amount c) m of the water-electrolyzed hydrogen, and the like.

The hydrogen supply unit 3 includes a hydrogen tank 3a configured to store the water-electrolyzed hydrogen generated by the water electrolyzer 2, and a flow control valve 3b provided on a piping between the hydrogen tank 3a and the gasifier 4. The hydrogen supply unit 3 supplies the water-electrolyzed hydrogen from the hydrogen tank 3a to the gasifier 4 by the pressure of the water-electrolyzed hydrogen stored in the hydrogen tank 3a, i.e., the internal pressure of the hydrogen tank 3a. The flow control valve 3b controls or regulates the supply amount (for example, mass flow rate) m of the water-electrolyzed hydrogen supplied from the hydrogen tank 3a to the gasifier 4.

The hydrogen supply unit 3 also includes sensors that measure the internal pressure of the hydrogen tank 3a, the supply amount $\underline{m}$ of the water-electrolyzed hydrogen supplied from the hydrogen tank 3a to the gasifier 4, and the like. When the internal pressure of the hydrogen tank 3a decreases below a lower limit pressure corresponding to a lower limit of the storage amount, it becomes impossible to supply the water-electrolyzed hydrogen from the hydrogen tank 3a to the gasifier 4. When the internal pressure of the hydrogen tank 3a increases above an upper limit pressure corresponding to an upper limit of the storage amount, it becomes impossible to store the water-electrolyzed hydrogen in the hydrogen tank 3a. The hydrogen supply unit 3 further includes a buffer tank that temporarily stores excess portion of the water-electrolyzed hydrogen until generation of the water-electrolyzed hydrogen by the water electrolyzer 2 is stopped after the storage amount of the hydrogen tank 3a has increased above the upper limit.

The hydrogen tank 3a is configured as a gas tank that is capable of storing hydrogen in a gas state. The higher the upper limit pressure of the storage amount of the hydrogen tank 3a is, the higher the volumetric storage efficiency of the water-electrolyzed hydrogen is. The hydrogen tank 3a may be configured as a liquid tank that is capable of storing hydrogen in a liquid state. In this case, the hydrogen supply unit 3 is required to further include a cooling device that converts hydrogen from a gas state to a liquid state. When hydrogen is stored in a liquid state, although additional energy is required for cooling and maintaining the cooled state, the water-electrolyzed hydrogen can be stored with a volumetric efficiency of about "800" times that for the case where the water-electrolyzed hydrogen is stored in a gas state. The hydrogen tank 3a may be constituted by a hydrogen storage alloy that stores hydrogen. In this case, the hydrogen supply unit 3 is required to further include a heating device that heats the hydrogen storage alloy to release hydrogen. When hydrogen is stored by the hydrogen storage alloy, the water-electrolyzed hydrogen can be stored with a volumetric efficiency of about "1000" times that for the case where the water-electrolyzed hydrogen is stored in a gas state.

The gasifier 4 mainly includes a gasification furnace, and performs gasification by heating the gasification furnace using the renewable power generated by the power generator 1 to generate the synthesis gas. Biomass such as rice husk, bagasse, or wood subjected to pretreatment such as drying and grinding, oxygen, and water (steam) are supplied to the gasification furnace of the gasifier 4, and the synthesis gas containing hydrogen and carbon monoxide is generated through reactions of the following formulas (i) to (v). The reactions of the formulas (ii) to (v) are equilibrium reactions.

$$C+O_2 \rightarrow CO_2 \qquad (i)$$

$$C+H_2O \rightarrow CO+H_2 \qquad (ii)$$

$$C+2H_2 \rightarrow CH_4 \qquad (iii)$$

$$C+CO_2 \rightarrow 2CO \qquad (iv)$$

$$CO+H_2O \rightarrow CO_2+H_2 \qquad (v)$$

Further, the water-electrolyzed hydrogen generated by the water electrolyzer 2 is supplied to the gasification furnace of the gasifier 4 through the hydrogen supply unit 3. The gasifier 4 is provided with sensors that measure a power consumption of the gasifier 4, a temperature and a pressure of the synthesis gas in the gasification furnace, a generation amount (for example, mass flow rate) of the synthesis gas, a partial pressure (concentration) of each gas component, and the like. The supply amount of biomass, oxygen, water, and water-electrolyzed hydrogen to the gasification furnace is controlled on the basis of measured values of these sensors.

By utilizing the water-electrolyzed hydrogen, the equilibrium reaction (shift reaction) of the formula (v) shifts in a direction that promotes the production of carbon monoxide and suppresses the production of carbon dioxide. Further, by controlling the supply amount $\underline{m}$ of the water-electrolyzed hydrogen generated by the water electrolyzer 2 and supplied by the hydrogen supply unit 3, the composition of the synthesis gas is adjusted to a composition suitable for the subsequent fuel production. For example, when producing the methanol fuel in the subsequent fuel production unit 5, the composition is adjusted so that the ratio (partial pressure ratio) of hydrogen to carbon monoxide in the synthesis gas becomes "2" in accordance with the methanol synthesis reaction of the following formula (vi).

$$CO+2H_2 \rightarrow CH_3OH \qquad (vi)$$

The fuel production unit 5 mainly includes a reactor and a distillation column. The synthesis gas generated by the gasifier 4 and subjected to posttreatment such as ash removal and desulfurization by washing is supplied to the reactor of the fuel production unit 5, and the methanol fuel is generated by the exothermic reaction of the formula (vi). More specifically, the product gas is distilled by heating the distillation column using the renewable power generated by the power generator 1, and the methanol fuel is obtained. The reactor and the distillation column of the fuel production unit 5 are respectively provided with sensors that measure a temperature and a pressure, a generation amount (for example, mass flow rate) and a concentration of the methanol fuel, and the like.

The fuel production system 100 further includes a compressor between the gasifier 4 and the fuel production unit 5, and the synthesis gas is delivered from the gasifier 4 to the fuel production unit 5 using the renewable power generated by the power generator 1. The fuel production system 100 further includes a sensor for measuring a power consumption of the compressor.

As described above, the fuel production system 100 can reduce emission of carbon dioxide as a whole by using the renewable energy. However, if the energy loss becomes large in the process of conversion of renewable energy, the energy loss and the fuel production cost of the whole system may increase. Therefore, the fuel production system 100 according to the embodiment of the present invention is configured as set out in the following so as to suppress the energy loss and the fuel production cost while suppressing emission of carbon dioxide in the fuel production by paying attention to the energy balance of the whole system.

Figure 2:
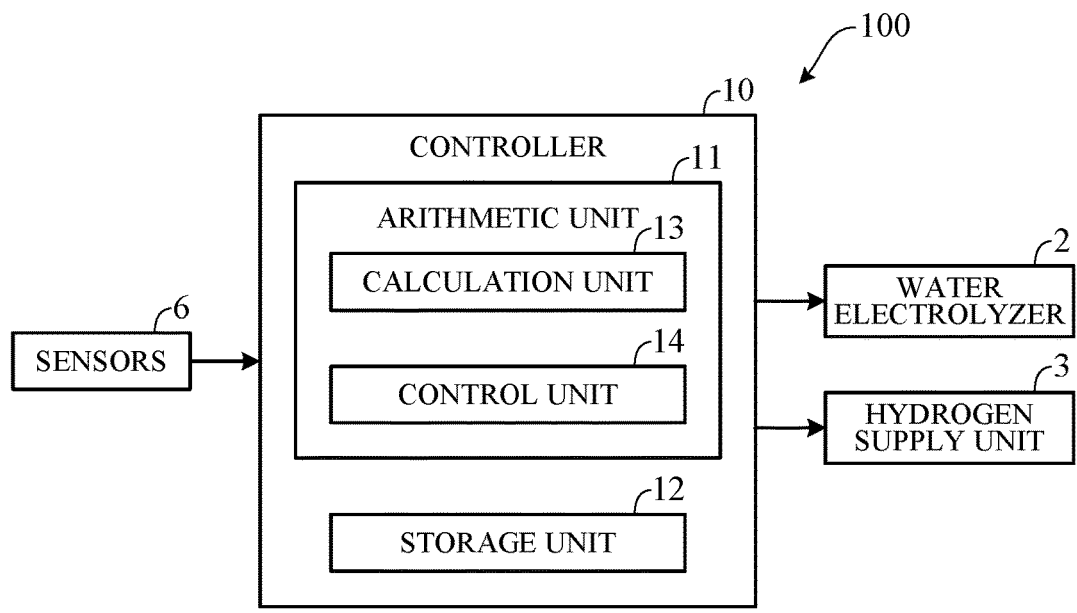
FIG. 2 is a block diagram schematically showing an example of main configuration of the fuel production system according to the embodiment of the present invention.

FIG. 2 is a block diagram schematically showing an example of main configuration of the fuel production system 100 according to the embodiment of the present invention. As shown in FIG. 2, the fuel production system 100 includes a controller 10. The controller 10 is connected with sensors 6 including the sensors described above, the water electrolyzer 2, and the hydrogen supply unit 3. The controller 10 controls operation of the water electrolyzer 2 and the hydrogen supply unit 3 by performing predetermined processing on the basis of signals from the sensors 6.

The controller 10 includes a computer including an arithmetic unit 11 such as CPU, a storage unit 12 such as ROM or RAM, and other peripheral circuits such as I/O interface (not shown). The storage unit 12 stores information such as various control programs and threshold values used in the programs. The arithmetic unit 11 includes, as a functional configuration, a calculation unit 13, and a control unit 14. In other words, the arithmetic unit 11 such as the CPU of the controller 10 functions as the calculation unit 13 and the control unit 14.

Figure 3:
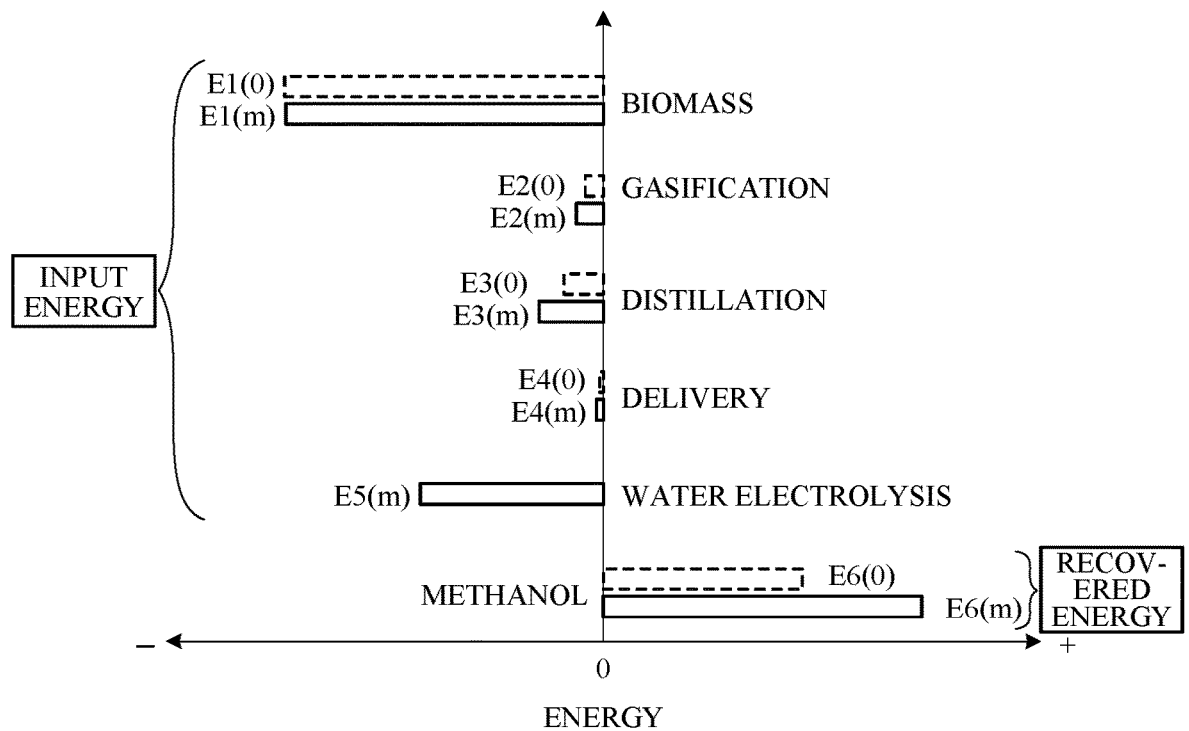
FIG. 3 is a diagram for explaining an energy balance of the fuel production system of FIG. 1.

FIG. 3 is a diagram for explaining the energy balance of the fuel production system 100, showing an example of input energy and recovered energy per unit amount of the raw material in the production of the methanol fuel using biomass as the raw material. The input energy includes an energy (calorific value) E1 possessed by a unit amount of biomass, energies E2 to E5 respectively required for gasification of the raw material (heating of the gasification furnace), distillation of the fuel, delivery of the synthesis gas, and electrolysis of water. The recovered energy includes an energy (calorific value) E6 possessed by the methanol fuel produced from a unit amount of biomass.

In FIG. 3, an energy E(0) for a case where the water-electrolyzed hydrogen is not used is shown as a broken line, and an energy E(m) for a case where the water-electrolyzed hydrogen is used is shown as a solid line, respectively. As shown in FIG. 3, in the case where the water-electrolyzed hydrogen is used, the energy E5(m) required for electrolysis is input depending on the supply amount m of the water-electrolyzed hydrogen and the energies E2(m) to E4(m) respectively required for gasification, distillation and delivery increase, while the energy E6(m) recovered as the methanol fuel increases.

The calculation unit 13 calculates the sum of energies E1(0) to E4(0) for the case where the water-electrolyzed hydrogen is not used as a standard input energy Ein(0), and calculates the sum of energies E1(m) to E5(m) for the case where the water-electrolyzed hydrogen is used as an input energy Ein(m), respectively, as the following formulas (vii) and (viii). The calculation unit 13 also calculates the energy E6(0) for the case where the water-electrolyzed hydrogen is not used as a standard recovered energy Eout(0), and calculates the energy E6(m) for the case where the water-electrolyzed hydrogen is used by as a recovered energy Eout(m), respectively, as the following formulas (ix) and (x).

$$Ein(0)=E1(0)+E2(0)+E3(0)+E4(0) \tag{vii}$$

$$Ein(m)=E1(m)+E2(m)+E3(m)+E4(m)+E5(m) \tag{viii}$$

$$Eout(0)=E6(0) \tag{ix}$$

$$Eout(m)=E6(m) \tag{x}$$

The energy E2 required for gasification of the raw material is calculated based on the standard reaction enthalpy and the amount of synthesis gas generated from the unit amount of biomass. The energy E2 can also be calculated based on the power consumption of the gasifier 4. The energy E3 required for distillation of the fuel is calculated based on the production amount and the concentration of the methanol fuel produced from the unit amount of biomass. The energy E3 can also be calculated based on the power consumption of the fuel production unit 5. The energy E4 required for delivery of the synthesis gas is calculated based on a compression work per unit amount and the amount of the synthesis gas generated from the unit amount of biomass. The energy E4 can also be calculated based on the power consumption of the compressor.

The energy E5 required for electrolysis of water is calculated based on the standard reaction enthalpy and the amount of the water-electrolyzed hydrogen generated from the unit amount of biomass and an electrolysis efficiency $\underline{p}$ of the water electrolyzer 2, as the following formula (xi). The electrolysis efficiency $\underline{p}$ of the water electrolyzer 2 is calculated based on the electrolysis voltage for the case where the electrolysis efficiency is 100% (for example, 1.48[V]) and the electrolysis voltage of the water electrolyzer 2, as the following formula (xii). The energy E5 required for electrolysis of water can also be calculated based on the power consumption of the water electrolyzer 2. It should be noted that, when water is electrolyzed using renewable power such as solar power or wind power, the power may be insufficient depending on weather conditions and the like, and the water electrolyzer 2 may not be able to operate at the rated capacity. In such case, the electrolysis efficiency $\underline{p}$ of the water electrolyzer 2 decreases.

$$E5=(\text{standard reaction enthalpy})\times(\text{amount of generated water-electrolyzed hydrogen})/p \tag{xi}$$

$$p=1.48/(\text{electrolysis voltage}) \tag{xii}$$

The calculation unit 13 calculates a difference $\Delta Ein(m)$ between the standard input energy Ein(0) and the input energy Ein(m), and calculates a difference $\Delta Eout(m)$ between the standard recovered energy Eout(0) and the recovered energy Eout(m), as the following formulas (xiii) and (xiv). The calculation unit 13 also calculates an energy conversion efficiency of the fuel production system 100, as the following formula (xv). The calculation unit 13 further calculates an evaluation value of the energy balance, as the following formula (xvi).

$$\Delta Ein(m)=Ein(m)-Ein(0) \tag{xiii}$$

$$\Delta Eout(m)=Eout(m)-Eout(0) \tag{xiv}$$

$$(\text{energy conversion efficiency})=Eout/Ein=E6/(E1+E2+E3+E4+E5) \tag{xv}$$

$$(\text{evaluation value of energy balance})=\Delta Eout(m)/\Delta Ein(m) \tag{xvi}$$

Figure 4:
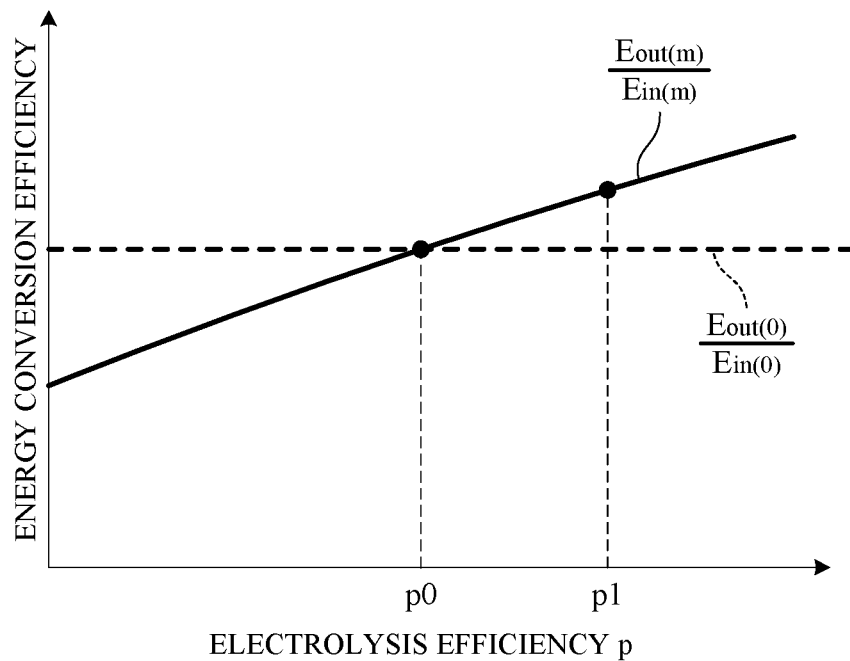
FIG. 4 is a diagram for explaining relationship between an electrolysis efficiency of a water electrolyzer of FIG. 1 and an energy conversion efficiency of the fuel production system.

FIG. 4 is a diagram for explaining relationship between the electrolysis efficiency $\overline{p}$ of the water electrolyzer 2 and the energy conversion efficiency of the fuel production system 100. In FIG. 4, the energy conversion efficiency Eout(0)/Ein(0) for the case where the water-electrolyzed hydrogen is not used is shown as a broken line, and the energy conversion efficiency Eout(m)/Ein(m) for the case where the water-electrolyzed hydrogen is used is shown as a solid line, respectively. As shown in FIG. 4, the energy conversion efficiency Eout(m)/Ein(m) of the fuel production system 100 for the case where the water-electrolyzed hydrogen is used increases as the electrolysis efficiency $\underline{p}$ of the water electrolyzer 2 increases. For this reason, under an operation condition of a predetermined electrolysis efficiency p0 or higher, the energy conversion efficiency increases by using the water-electrolyzed hydrogen as compared with the case where the water-electrolyzed hydrogen is not used. On the other hand, under an operation condition of the predetermined electrolysis efficiency p0 or lower, the energy conversion efficiency decreases by using the water-electrolyzed hydrogen as compared with the case where the water-electrolyzed hydrogen is not used. The threshold value of the electrolysis efficiency p (predetermined electrolysis efficiency p0), in which the energy conversion efficiency Eout(m)/Ein(m) for the case where the water-electrolyzed hydrogen is used becomes higher than the energy conversion efficiency Eout(0)/Ein(0) for the case where the water-electrolyzed hydrogen is not used, varies depending on the generation amount of the water-electrolyzed hydrogen. The storage unit 12 stores information about the predetermined electrolysis efficiency p0 measured in advance.

Figure 5:
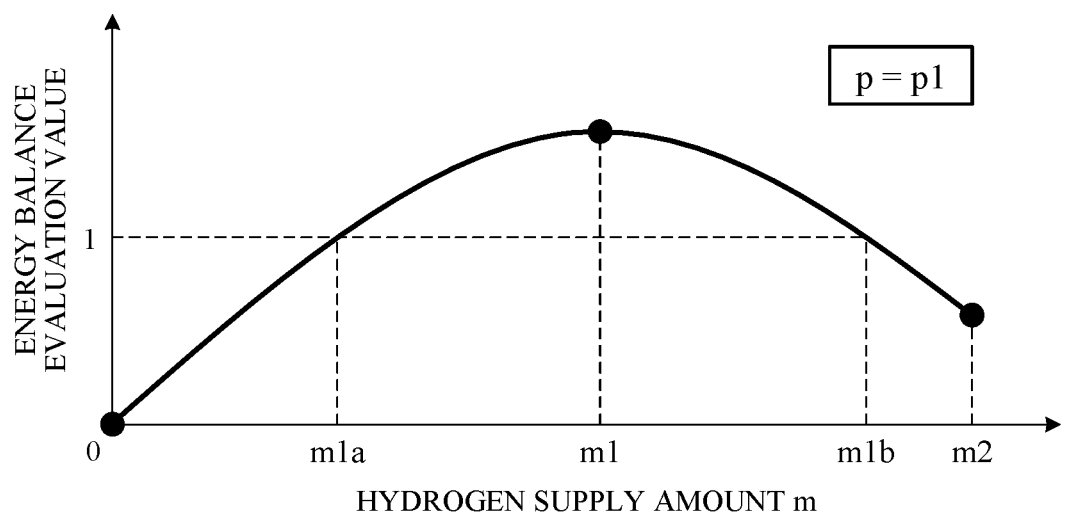
FIG. 5 is a diagram for explaining relationship between a hydrogen supply amount by a hydrogen supply unit of FIG. 1 and an evaluation value of the energy balance of the fuel production system.

FIG. 5 is a diagram for explaining relationship between the supply amount m of the water-electrolyzed hydrogen supplied by the hydrogen supply unit 3 and the evaluation value of the energy balance of the fuel production system 100. FIG. 5 shows an example of the evaluation value when changing the supply amount m of the water-electrolyzed hydrogen under an operation condition corresponding to the electrolysis efficiency p1 of FIG. 4. As shown in FIG. 5, the supply amount m of the water-electrolyzed hydrogen has an optimal quantity m1 depending on operation conditions such as the electrolysis efficiency p and the like. When controlling the supply amount m of the water-electrolyzed hydrogen within an appropriate range m1a to m1b where the evaluation value of the energy balance is "1" or higher, the energy conversion efficiency increases as compared with the case where the water-electrolyzed hydrogen is not used. On the other hand, when supplying the water-electrolyzed hydrogen of an excess amount m2 exceeding the appropriate range m1a to m1b (for example, "1.5" times the optimal quantity m1), the evaluation value of the energy balance decreases below "1" and the energy conversion efficiency decreases as compared with the case where the water-electrolyzed hydrogen is not used.

Figure 6A:
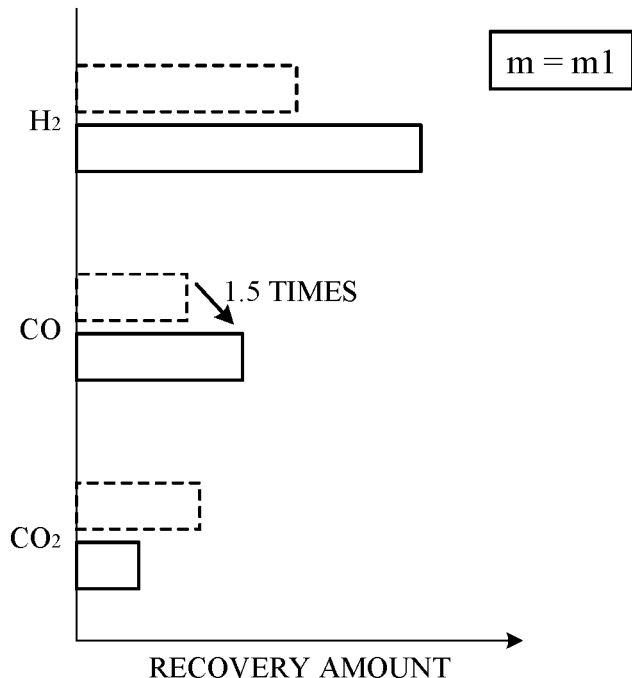
FIG. 6A is a diagram showing an example of a recovery amount of each gas component from a gasifier of FIG. 1.
Figure 6B:
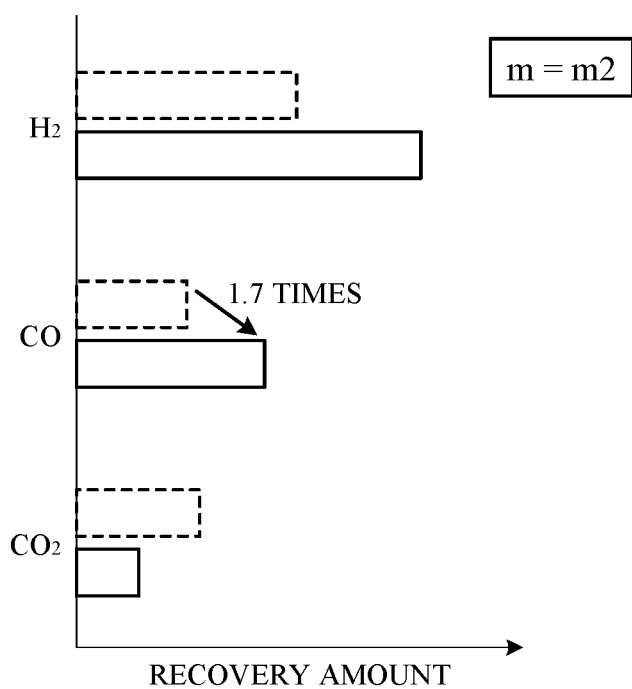
FIG. 6B is a diagram showing another example of the recovery amount of each gas component from the gasifier of FIG. 1.

FIGS. 6A and 6B are diagrams showing an example of the recovery amount (for example, mass flow rate) of each gas component from the gasifier 4. In FIGS. 6A and 6B, the recovery amount for the case where the water-electrolyzed hydrogen is not used is shown as a broken line, and the recovery amount for the case where the water-electrolyzed hydrogen is used is shown as a solid line, respectively. FIG. 6A shows an example of the recovery amount of each gas component for a case where the supply amount m of the water-electrolyzed hydrogen in FIG. 5 is the optimal quantity m1, and FIG. 6B shows an example of the recovery amount of each gas component for a case where the supply amount m of the water-electrolyzed hydrogen is the excess amount m2.

In the example shown in FIG. 6A, the supply amount m of the water-electrolyzed hydrogen has been adjusted to the optimal quantity m1, and the recovery amount of carbon monoxide corresponding to the production amount of the methanol fuel has increased by "1.5" times that for the case where the water-electrolyzed hydrogen is not used. On the other hand, in the example shown in FIG. 6B, the supply amount m of the water-electrolyzed hydrogen has been adjusted to the excess amount m2, which is "1.5" times the optimal quantity m1, and the recovery amount of carbon monoxide has increased by "1.7" times that for the case where the water-electrolyzed hydrogen is not used. Comparing the example of FIG. 6A with the example of FIG. 6B, the supply amount m of the water-electrolyzed hydrogen corresponding to the input energy increases by "1.5" times, whereas the recovery amount of carbon monoxide corresponding to the recovered energy increases only by a factor of about "1.1" times. As described above, if the supply amount m of the water-electrolyzed hydrogen increases beyond the appropriate range, the energy conversion efficiency decreases more than in the case where the water-electrolyzed hydrogen is not used.

The calculation unit 13 further calculates a cost C and a profit B for the case where the water-electrolyzed hydrogen is used, and calculates an evaluation value of the cost merit ε(m) for the case where the water-electrolyzed hydrogen is used as the following formula (xvii).

$$\varepsilon(m) = C/B \qquad (xvii)$$

The cost C generated by using the water-electrolyzed hydrogen is calculated based on, for example, the power consumption of the water electrolyzer 2 for water electrolysis, the gasifier 4 for gasification of the biomass, the fuel production unit 5 for distillation of the methanol fuel, and the compressor for delivery of the synthesis gas. In this case, the cost C generated by using the water-electrolyzed hydrogen is calculated based on the power consumption for the case where the water-electrolyzed hydrogen is not used and for the case where the water-electrolyzed hydrogen is used respectively, and the unit price of electric power.

The profit B obtained by using the water-electrolyzed hydrogen is specifically calculated as a profit obtained due to an increase in the production amount of the methanol fuel. In this case, the profit B obtained by using the water-electrolyzed hydrogen is calculate based on the production amount of the methanol fuel for the case where the water-electrolyzed hydrogen is not used and for the case where the water-electrolyzed hydrogen is used respectively, and the unit price of the methanol fuel.

The control unit 14 controls operation of the water electrolyzer 2 and the flow control valve 3b of the hydrogen supply unit 3 based on the electrolysis efficiency p of the water electrolyzer 2 calculated by the calculation unit 13, the evaluation value of the cost merit ε(m), and the internal pressure of the hydrogen tank 3a measured or detected by the sensors 6. More specifically, the control unit 14 controls ON-OFF operation of the water electrolyzer 2 to generate the water-electrolyzed hydrogen only when the energy conversion efficiency increases as compared with the case where the water-electrolyzed hydrogen is not used based on the electrolysis efficiency p of the water electrolyzer 2. The control unit 14 also controls ON-OFF operation of the water electrolyzer 2 to generate the water-electrolyzed hydrogen only when there is a cost merit is generated by using the water-electrolyzed hydrogen based on the evaluation value of the cost merit ε(m). The control unit 14 further controls operation of the flow control valve 3b so as to maintain the storage amount of the water-electrolyzed hydrogen stored in the hydrogen supply unit 3 to an appropriate amount between the lower limit and the upper limit based on the internal pressure of the hydrogen tank 3a.

Figure 7:
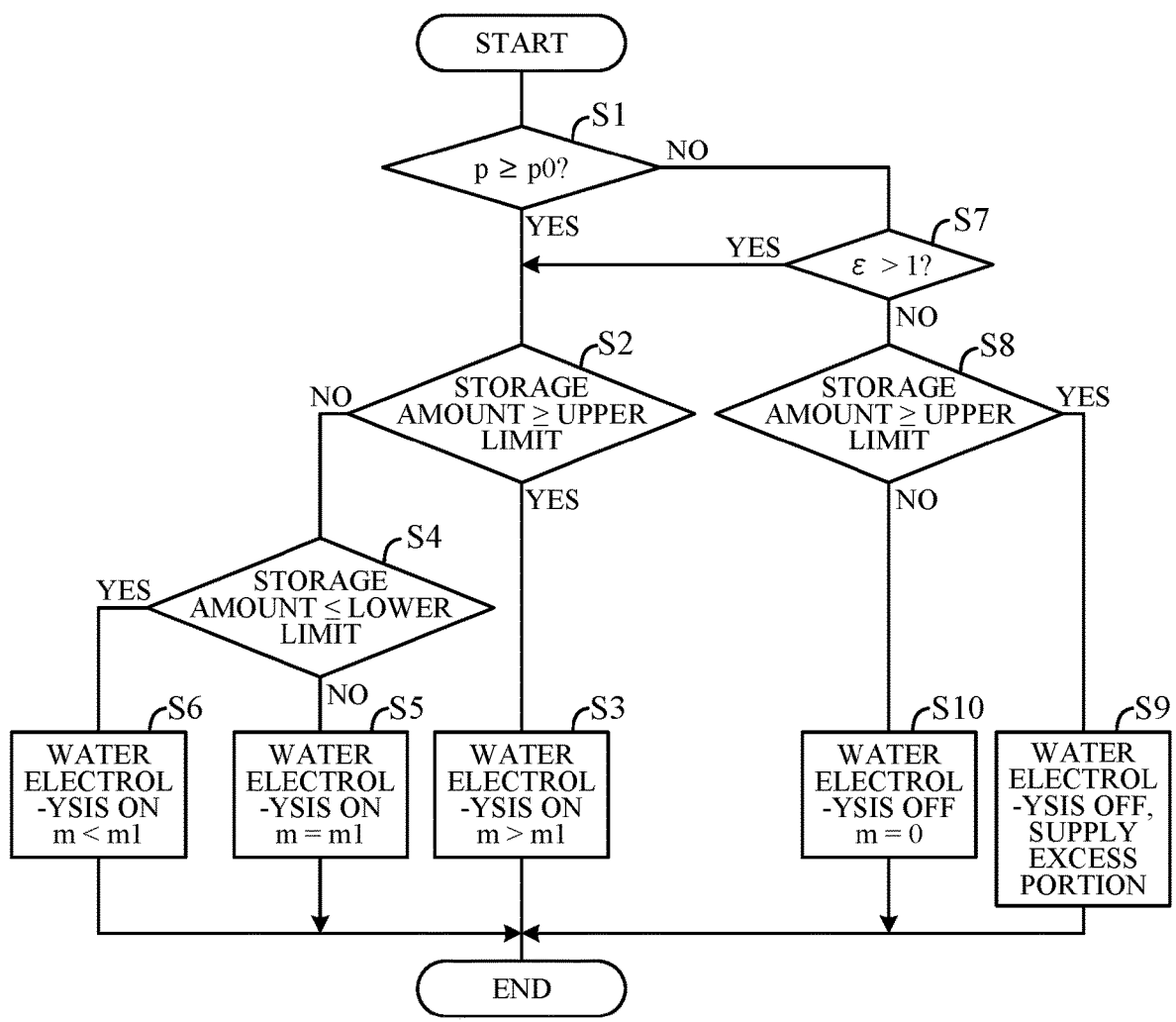
FIG. 7 is a flowchart showing an example of processing performed by a controller of FIG. 2.

FIG. 7 is a flowchart showing an example of processing performed by the arithmetic unit 11 of the controller 10. The processing of the FIG. 7 is started, for example, when the fuel production system 100 is powered on, and is repeated at a predetermined cycle. In the processing of FIG. 7, first, in S1 (S: processing step), it is determined whether the electrolysis efficiency p of the water electrolyzer 2 is equal to or higher than the predetermined electrolysis efficiency p0 corresponding to the current generation amount of the water-electrolyzed hydrogen (FIG. 4).

When S1 is affirmative, it is determined that the operation condition is an operation condition in which the energy conversion efficiency increases by using the water-electrolyzed hydrogen, and the process proceeds to S2, in which it is determined whether the storage amount of the hydrogen tank 3a is equal to or larger than the upper limit. When S2 is affirmative, the process proceeds to S3, in which the supply amount m of the water-electrolyzed hydrogen from the hydrogen tank 3a to the gasifier 4 is adjusted to be larger than the optimal amount m1 so that water electrolysis by the water electrolyzer 2 can be continued. Water electrolysis by the water electrolyzer 2 may be stopped and the renewable power generated by the power generator 1 may be sold to the commercial power grid. When S2 is negative, the process proceeds to S4, in which it is determined whether the storage amount of the hydrogen tank 3a is equal to or smaller than the lower limit. When S4 is negative, the process proceeds to S5, in which water electrolysis by the water electrolyzer 2 is continued with the supply amount m of the water-electrolyzed hydrogen as the optimal amount m1. When S4 is affirmative, the process proceeds to S6, in which the supply amount m of the water-electrolyzed hydrogen is adjusted to be smaller than the optimal amount m1 so that supply of the water-electrolyzed hydrogen can be continued. The power consumption of the water electrolyzer 2 may be supplemented by purchasing power from the commercial power grid.

When S1 is negative, it is determined that the operation condition is an operation condition in which the energy conversion efficiency decreases by using the water-electrolyzed hydrogen, and the process proceeds to S7, in which it is determined whether the evaluation value of the cost merit ε(m) by using the water-electrolyzed hydrogen exceeds "1". When S7 is affirmative, it is determined that the operation condition is an operation condition in which the energy conversion efficiency decreases but there is a cost merit, and the process proceeds to S2. On the other hand, when S7 is negative, it is determined that the operation condition is an operation condition in which the energy conversion efficiency decreases and there are no cost merit by using the water-electrolyzed hydrogen, and the process proceeds to S8.

In S8, it is determined whether the storage amount of the hydrogen tank 3a is equal to or larger than the upper limit. When S8 is affirmative, the process proceeds to S9, in which water electrolysis by the water electrolyzer 2 is stopped and the excess portion of the water-electrolyzed hydrogen temporarily stored in the buffer tank of the hydrogen supply unit 3 is supplied to the gasifier 4. In this case, the renewable power generated by the power generator 1 may be sold to the commercial power grid. When S8 is negative, the process proceeds to S10, in which water electrolysis by the water electrolyzer 2 is stopped and supply of the water-electrolyzed hydrogen from the hydrogen tank 3a to the gasifier 4 is stopped. In this case, the renewable power generated by the power generator 1 may be sold to the commercial power grid.

As described above, by switching ON and OFF the water electrolyzer 2 depending on the monitoring result of the electrolysis efficiency p of the water electrolyzer 2 and the evaluation value of the cost merit ε(m) (S1, S7), it becomes possible to operate the fuel production system 100 in an operation range where energy loss and fuel production cost is suppressed. That is, by controlling the water electrolyzer 2 so as to utilize the water-electrolyzed hydrogen only when the energy conversion efficiency increases or the cost merit occurs, it becomes possible to suppress the energy loss and fuel production cost (S3, S5, S6, S9, and S10).

The present embodiment can achieve advantages and effects such as the following:

(1) The fuel production system 100 includes: the gasifier 4 configured to generate the synthesis gas containing hydrogen and carbon monoxide from biomass; the fuel production unit 5 configured to produce the methanol fuel from the synthesis gas generated by the gasifier 4; the water electrolyzer 2 configured to electrolyze water to generate water-electrolyzed hydrogen; the hydrogen supply unit 3 configured to supply the water-electrolyzed hydrogen generated by the water electrolyzer 2 to the gasifier 4; the calculation unit 13 configured to calculate the input energy Ein(m) based on the energy E1 possessed by the biomass, the energy E5 consumed by the water electrolyzer 2 when generating the water-electrolyzed hydrogen, the energy E2 consumed by the gasifier 4 when generating the synthesis gas, and the energy E3 consumed by the fuel production unit 5 when producing the methanol fuel, and configured to calculate the recovered energy Eout(m) based on the energy E6 possessed by the methanol fuel produced by the fuel production unit 5; and the control unit 14 configured to control the water electrolyzer 2 based on the input energy Ein(m) and the recovered energy Eout(m) calculated by the calculation unit 13 (FIGS. 1 to 3).

In other words, the operation condition is monitored so that the energy conversion efficiency Eout(m)/Ein(m), which indicates the ratio of the recovered energy Eout(m) to the input energy Ein(m), increases above the energy conversion efficiency Eout(0)/Ein(0) for the case where the water-electrolyzed hydrogen is not used. For example, monitoring whether the electrolysis efficiency p of the water electrolyzer 2 is equal to or higher than the predetermined electrolysis efficiency p0 for a case where the energy conversion efficiency Eout/Ein increases as compared with the case where the water-electrolyzed hydrogen is not used. With this, it becomes possible to suppress energy loss and fuel production cost in the fuel production by monitoring the energy conversion efficiency of the entire fuel production system 100 through the input energy Ein(m) and the recovered energy Eout(m). That is, when the energy loss in the conversion process of the renewable energy increases depending on weather conditions and the like, energy loss and fuel production cost as a whole system increase. Therefore, depending on the monitoring result of the energy conversion efficiency, for example, by controlling the water electrolyzer 2 to generate the water-electrolyzed hydrogen only when the energy conversion efficiency increases as compared with the case where the water-electrolyzed hydrogen is not used, it becomes possible to suppress the energy loss and the fuel production cost.

(2) The calculation unit 13 further calculates the cost C required for obtaining the energy E5, the energy E2, and the energy E3, and calculates the profit B obtained from the methanol fuel produced by the fuel production unit 5. The control unit 14 further controls the water electrolyzer 2 based on the cost C and the profit B calculated by the calculation unit 13. For example, the control unit 14 controls the water electrolyzer 2 as to generate the water-electrolyzed hydrogen only when the evaluation value of the cost merit ε(m), which indicates the ratio of the profit B to the cost C, exceeds "1". With this, it becomes possible to suppress fuel production cost of the fuel production system 100 by controlling the water electrolyzer 2 to generate the water-electrolyzed hydrogen only when there is a cost merit by using the water-electrolyzed hydrogen.

(3) The calculation unit 13 calculates the energy E5 consumed by the water electrolyzer 2 when generating the water-electrolyzed hydrogen based on the generation amount of the water-electrolyzed hydrogen generated by the water electrolyzer 2 and the electrolysis efficiency p of the water electrolyzer 2. With this, it becomes possible to calculate the electrolysis efficiency p based on the actually measured electrolysis voltage to calculate the energy E5 consumed by the water electrolyzer 2 when generating the water-electrolyzed hydrogen.

(4) The calculation unit 13 calculates the energy E5 consumed by the water electrolyzer 2 when generating the water-electrolyzed hydrogen based on the power consumption consumed by the water electrolyzer 2 when generating the water-electrolyzed hydrogen. With this, it becomes possible to calculate the energy E5 consumed by the water electrolyzer 2 when generating the water-electrolyzed hydrogen based on the actually measured power consumption.

(5) The water electrolyzer 2 electrolyzes water using renewable power. When using renewable power such as solar power or wind power, the power may be insufficient depending on weather conditions and the like, and the water electrolyzer 2 may not be able to operate at the rated capacity. In such case, the electrolysis efficiency p of the water electrolyzer 2 may decrease and the energy conversion efficiency of the whole fuel production system 100 rather decreases by using the water-electrolyzed hydrogen. By monitoring the energy conversion efficiency of the whole fuel production system 100 through the input energy Ein(m) and the recovered energy Eout(m), it becomes possible to properly suppress the energy loss in the fuel production.

Although, in the above, for example, in FIG. 1, the gasifier 4 generates the synthesis gas from the biomass, a synthesis gas generation unit configured to generate synthesis gas containing hydrogen and carbon monoxide from carbon-containing raw material is not limited to the above described configuration. For example, the synthesis gas generation unit may separate and recover carbon dioxide from the factory exhaust gas or the like by DAC (Direct Air Capture) and generate carbon monoxide and water from the recovered carbon dioxide and the water-electrolyzed hydrogen by a reverse equilibrium reaction (reverse shift reaction) of the formula (v).

Although, in the above, for example, in FIG. 1, the fuel production unit 5 produces the methanol fuel, a fuel production unit configured to produce fuel from the synthesis gas is not limited to the above described configuration. For example, the fuel production unit may further synthesize gasoline fuel from methanol by MTG (methanol-to-gasoline) method, or synthesize diesel fuel from the synthesis gas by FT (Fischer-Tropsch) method.

Although, in the above, the renewable power is used for gasification of raw materials (heating of the gasification furnace) and distillation of the fuel, other heat sources such as waste heat or the like may be used for these. In this case, a third energy consumed by the synthesis gas generation unit when generating the synthesis gas and a fourth energy consumed by the fuel production unit when producing the fuel is calculated based on the amount of heat required for gasification and distillation and the unit cost of heat.

Although, in the above, for example, in FIG. 3, a specific example of energies has been shown and described as the input energy and the recovered energy of the fuel production system 100, an input energy and a recovered energy are not limited to these energies.

Although, in the above, for example, in FIG. 1, all of the water-electrolyzed hydrogen generated by the water electrolyzer 2 is supplied to the gasifier 4, a hydrogen supply unit configured to supply the water-electrolyzed hydrogen generated by the water electrolyzer to the synthesis gas generation unit is not limited to the above described configuration. For example, the hydrogen supply unit may include a hydrogen tank for storing the water-electrolyzed hydrogen, a flow control valve for controlling flow rate of the water-electrolyzed hydrogen supplied to the gasifier, or the like. The operation of the water electrolyzer 2 may be stopped when the electrolysis efficiency p of the water electrolyzer 2 decreases below the predetermined electrolysis efficiency p0 depending on weather conditions and the like.

The above embodiment can be combined as desired with one or more of the aforesaid modifications. The modifications can also be combined with one another.

According to the present invention, it becomes possible to suppress the energy loss and the fuel production cost while in the fuel production.

Above, while the present invention has been described with reference to the preferred embodiments thereof, it will be understood, by those skilled in the art, that various changes and modifications may be made thereto without departing from the scope of the appended claims.

The invention claimed is:

1. A fuel production system, comprising:
a synthesis gas generation unit configured to generate synthesis gas containing hydrogen and carbon monoxide from carbon-containing raw material;
a fuel production unit configured to produce fuel from the synthesis gas generated by the synthesis gas generation unit;
a water electrolyzer configured to electrolyze water to generate water-electrolyzed hydrogen;
a hydrogen supply unit configured to supply the water-electrolyzed hydrogen generated by the water electrolyzer to the synthesis gas generation unit; and
a controller including an arithmetic unit and a storage unit, wherein
the controller is configured to perform:
calculating an input energy based on a first energy possessed by the carbon-containing raw material, a second energy consumed by the water electrolyzer when generating the water-electrolyzed hydrogen, a third energy consumed by the synthesis gas generation unit when generating the synthesis gas, and a fourth energy consumed by the fuel production unit when producing the fuel;
calculating a recovered energy based on a fifth energy possessed by the fuel produced by the fuel production unit;
monitoring whether an electrolysis efficiency of the water electrolyzer is equal to or higher than a predetermined electrolysis efficiency in which a ratio of the recovered energy to the input energy increases as compared with a case where the water-electrolyzed hydrogen is not generated and supplied; and
controlling the water electrolyzer so as to generate the water-electrolyzed hydrogen when the electrolysis efficiency is equal to or higher than the predetermined electrolysis efficiency.

2. The fuel production system according to claim 1, wherein
the controller is configured to perform:
calculating a cost required for obtaining the second energy, the third energy, and the fourth energy;
calculating a profit obtained from the fuel produced by the fuel production unit; and
controlling the water electrolyzer so as to generate the water-electrolyzed hydrogen when a ratio of the profit to the cost exceeds one.

3. The fuel production system according to claim 1, wherein
the controller is configured to perform:
calculating the second energy based on a generation amount of the water-electrolyzed hydrogen generated by the water electrolyzer and the electrolysis efficiency of the water electrolyzer.

4. The fuel production system according to claim 1, wherein
the controller is configured to perform:
calculating the second energy based on a power consumption consumed by the water electrolyzer when generating the water-electrolyzed hydrogen.

5. The fuel production system according to claim 1, wherein
the water electrolyzer electrolyzes the water using renewable power.

* * * * *